United States Patent
Nita

[11] Patent Number: 5,989,208
[45] Date of Patent: Nov. 23, 1999

[54] THERAPEUTIC ULTRASOUND SYSTEM

[76] Inventor: Henry Nita, 26051 Malaga La., Mission Viejo, Calif. 92692

[21] Appl. No.: 08/857,416

[22] Filed: May 16, 1997

[51] Int. Cl.[6] .................................................. A61B 17/20
[52] U.S. Cl. .......................... 604/22; 600/467; 600/470
[58] Field of Search ................................ 604/19–22, 96, 604/102, 113, 282, 283, 905, 912, 915, 916; 600/437, 459, 462, 466, 467, 470, 471; 601/2; 128/200.16; 433/86

[56] References Cited

U.S. PATENT DOCUMENTS

| | | | |
|---|---|---|---|
| 4,417,578 | 11/1983 | Banko | 604/22 |
| 4,425,115 | 1/1984 | Wuchinich | 604/22 |
| 4,572,184 | 2/1986 | Stohl et al. | |
| 4,721,117 | 1/1988 | Mar et al. | 604/170 |
| 4,838,853 | 6/1989 | Parisi | 604/22 |
| 4,920,954 | 5/1990 | Alliger et al. | 606/128 |
| 5,026,384 | 6/1991 | Farr et al. | 606/159 |
| 5,046,503 | 9/1991 | Schneiderman | 600/470 |
| 5,127,917 | 7/1992 | Niederhauser et al. | 606/191 |
| 5,156,143 | 10/1992 | Bocquet et al. | 128/24 AA |
| 5,180,363 | 1/1993 | Idemoto et al. | 202/32 |
| 5,195,955 | 3/1993 | Don Michael | 604/22 |
| 5,226,421 | 7/1993 | Frisbie et al. | 600/470 |
| 5,242,385 | 9/1993 | Strukel | 604/22 |
| 5,248,296 | 9/1993 | Alliger | 604/22 |
| 5,255,669 | 10/1993 | Kubota et al. | 128/24 AA |
| 5,267,954 | 12/1993 | Nita | 604/22 |
| 5,269,297 | 12/1993 | Weng et al. | 128/24 AA |
| 5,304,115 | 4/1994 | Pflueger et al. | 604/22 |
| 5,312,328 | 5/1994 | Nita et al. | 604/22 |
| 5,318,570 | 6/1994 | Hood et al. | 606/99 |
| 5,378,234 | 1/1995 | Hammerslag et al. | 604/95 |
| 5,380,274 | 1/1995 | Nita | 604/22 |
| 5,382,228 | 1/1995 | Nita et al. | 604/22 |
| 5,383,460 | 1/1995 | Jang et al. | 128/660.03 |
| 5,397,293 | 3/1995 | Alliger et al. | 601/2 |
| 5,417,672 | 5/1995 | Nita et al. | 604/283 |
| 5,421,923 | 6/1995 | Clarke et al. | 156/73.1 |
| 5,449,369 | 9/1995 | Imran | 606/159 |
| 5,451,209 | 9/1995 | Ainsworth et al. | 604/96 |
| 5,484,398 | 1/1996 | Stoddard | 604/22 |
| 5,507,738 | 4/1996 | Ciervo | 606/1 |
| 5,527,273 | 6/1996 | Manna et al. | 604/22 |

(List continued on next page.)

FOREIGN PATENT DOCUMENTS

| | | |
|---|---|---|
| 0005719 | 12/1979 | European Pat. Off. . |
| 0376562 | 7/1990 | European Pat. Off. . |
| 0394583 | 10/1990 | European Pat. Off. . |
| 0443256 | 8/1991 | European Pat. Off. . |
| 0541249 | 5/1993 | European Pat. Off. . |
| 2256127 | 5/1974 | Germany . |
| 1106957 | 3/1968 | United Kingdom . |
| 9001300 | 2/1990 | WIPO . |
| 9004362 | 5/1990 | WIPO . |
| 9107917 | 6/1991 | WIPO . |
| 9316646 | 9/1993 | WIPO . |
| WO9412140 | 6/1994 | WIPO . |
| 9414382 | 7/1994 | WIPO . |
| WO9509571 | 4/1995 | WIPO . |

*Primary Examiner*—Corrine McDermott
*Assistant Examiner*—Sharon Finkel
*Attorney, Agent, or Firm*—Raymond Sun

[57] ABSTRACT

An ultrasound system is disclosed having a catheter including an elongate flexible catheter body having at least one lumen extending longitudinally therethrough. The catheter further includes an ultrasound transmission member extending longitudinally through the lumen of the catheter body, the ultrasound transmission member having a proximal end connectable to an ultrasound transducer. The catheter also includes a distal head positioned on the distal end of the ultrasound transmission member. The catheter also has a coil with a proximal end connected to the distal end of the catheter body, and a distal end connected to the distal head. The coil defines a lumen communicating with the lumen of the catheter body. The ultrasound system also includes a sonic connector for coupling the ultrasound transmission member to the transducer. Different configurations are disclosed for the distal head and the ultrasound transmission member.

21 Claims, 5 Drawing Sheets

U.S. PATENT DOCUMENTS

| | | | |
|---|---|---|---|
| 5,540,656 | 7/1996 | Pflueger et al. | 604/22 |
| 5,542,917 | 8/1996 | Nita et al. | 604/22 |
| 5,626,593 | 5/1997 | Imran | 606/159 |
| 5,649,935 | 7/1997 | Kremer et al. | 606/128 |
| 5,658,282 | 8/1997 | Daw et al. | 606/49 |
| 5,695,507 | 12/1997 | Auth et al. | 606/159 |
| 5,738,100 | 4/1998 | Yagami et al. | 128/662.06 |

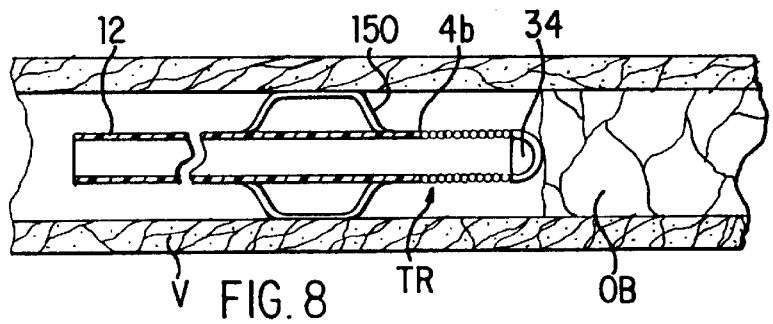
FIG. 8
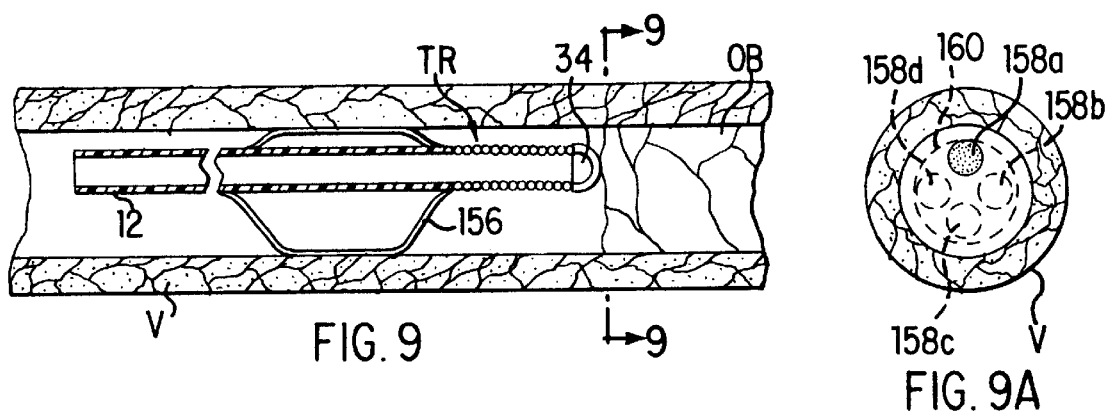
FIG. 9
FIG. 9A
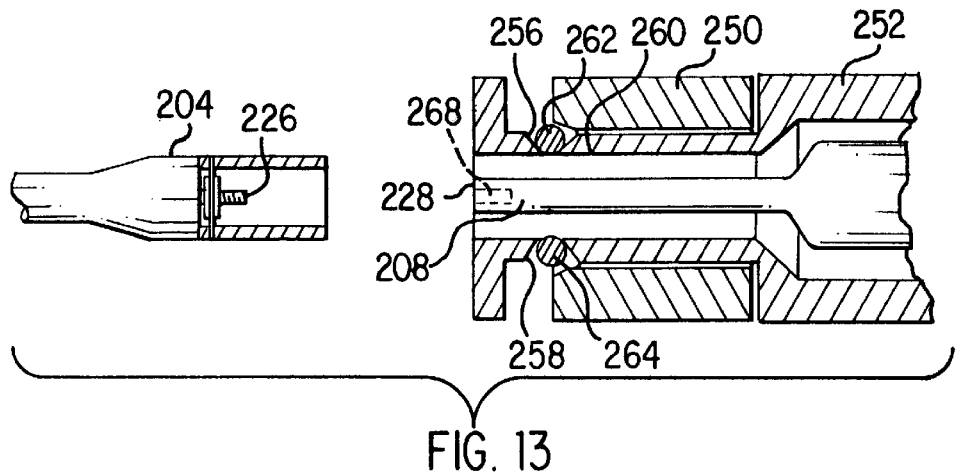
FIG. 13
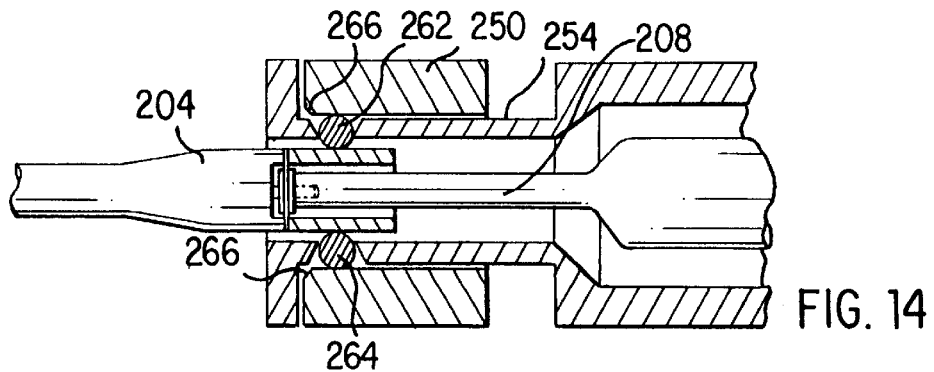
FIG. 14

THERAPEUTIC ULTRASOUND SYSTEM

BACKGROUND OF THE INVENTION

1. Field of the Invention

The present invention pertains to medical equipment, and more particularly, to a therapeutic ultrasound system for ablating obstructions within tubular anatomical structures such as blood vessels, and for myocardial revascularization of heart tissue.

2. Description of the Prior Art

A number of ultrasound systems and devices have heretofore been proposed for use in ablating or removing obstructive material from blood vessels. However, all of these systems and devices generally encounter three types of problems which are not always adequately addressed by these systems and devices.

The first type of problem relates generally to the effective transmission of ultrasound energy from an ultrasound source to the distal tip of the device where the ultrasound energy is applied to ablate or remove obstructive material. Since the ultrasound source, such as a transducer, is usually located outside the human body, it is necessary to deliver the ultrasound energy over a long distance, such as about 150 cm, along an ultrasound transmission wire from the source to the distal tip. Attenuation of the acoustical energy along the length of the transmission wire means that the energy reaching the distal tip is reduced. To ensure that sufficient energy reaches the distal tip, a greater amount of energy must be delivered along the transmission wire from the source to the distal tip. This transmission of increased energy along the transmission wire may increase the fatigue experienced by the transmission wire at certain critical locations, such as at the connection between the transducer and the transmission wire.

The second type of problem relates to the need for accurately positioning the ultrasound device inside a patient's vasculature, and in particular, where the vasculature contains smaller and more tortuous vessels. To address this need, flexible and low-profile ultrasound devices have been provided which allow the device to be navigated through small and tortuous vessels. To provide a more flexible ultrasound transmission wire for such flexible and low-profile ultrasound devices, the cross-sectional area of the transmission wire is usually tapered or narrowed near the distal end. While such tapering or narrowing decreases rigidity and improves bendability, it causes a significant increase in amplitude of the ultrasound energy being transmitted through the tapered or narrowed region, thereby increasing the likelihood of breakage or fracture of the transmission wire due to the increased transverse motion. These transverse micro-motions are produced by the transducer and further amplified by any tapering or narrowing of the transmission wire.

The third type of problem relates to the application of undesirable external forces to the connection between the transducer and the transmission wire during clinical use of the ultrasound device. Such forces may be applied during the bending, pushing, torquing and pressing of the ultrasound device as the device is being introduced and navigated along the patient's vasculature. These forces may result in the overloading of the transducer, which may minimize the amount of ultrasound energy delivered to the distal end of the catheter device 10. These forces may also increase transducer output to compensate for this unwanted load, which may result in transducer overheating and hardware failure.

The above-described problems are similarly experienced by ultrasound systems where ultrasound energy is used to percuataneously revascularize the myocardium of the heart.

Thus, there still exists a need in the art for improved ultrasound systems having ultrasound devices or catheters which address the aforementioned problems. In particular, there is a need for ultrasound devices that: (1) are sufficiently flexible to be inserted into and advanced along both small and tortuous blood vessels, (2) provide an improved connection between the transmission member and the transducer, (3) provide an improved ultrasound transmission member which combines strength, elasticity and effective transmission properties, (4) provide improved configurations for the distal end that are effective in ablating or removing occlusive material in vessels, and (5) mitigate the impact of undesirable loading on the connection between the transmission member and the transducer.

SUMMARY OF THE DISCLOSURE

In order to accomplish the objects of the present invention, there is provided an ultrasound system having a catheter including an elongate flexible catheter body having at least one lumen extending longitudinally therethrough. The catheter further includes an ultrasound transmission member extending longitudinally through the lumen of the catheter body, the ultrasound transmission member having a proximal end connectable to a separate ultrasound generating device. The catheter also includes a distal head positioned on the distal end of the ultrasound transmission member.

According to one embodiment, the ultrasound transmission member is made from a material that includes nickel having an atomic weight ranging from 50.50 to 51.50.

According to another embodiment, the present invention provides a coil having a proximal end connected to the distal end of the catheter body, and a distal end connected to the distal head. The coil defines a lumen communicating with the lumen of the catheter body. The coil may braided, cross-wound, or multilead. An inner tube extends inside the lumens of the catheter body and the coil, the inner tube having a proximal end connected to the catheter body and a free distal end to define a spacing between the distal end of the inner tube and the distal head. The distal head may be provided with a fluid outflow channel extending therethrough and communicating with the lumens of the catheter body and the coil, so that drugs may be aspirated through the spacing and the fluid outflow channel. According to a different embodiment of the present invention, the distal end of the inner tube may be connected to the distal head so that no spacing is defined.

The present invention also provides a distal head with a generally cylindrical proximal portion with a bore for receiving the distal end of the ultrasound transmission member. In one embodiment, the distal head further includes a rounded distal portion having a narrowed tip extending distally therefrom. In another embodiment, the distal head further includes a central narrowed tip and an annular ridge separated by a concave region.

The present invention also provides the ultrasound transmission member in a number of alternative configurations. In one embodiment, the ultrasound transmission member has a proximal region with a larger dimension than an intermediate region, and a distal region with a smaller dimension than the intermediate region. In another embodiment, the ultrasound transmission member has a proximal region and a distal region which is continuously tapered until it reaches a conical distal tip. In yet another embodiment, the ultrasound transmission member has a proximal region, a distal end, and an intermediate region between the proximal region and the distal end. The distal end has a ball having a diameter which is larger than the dimension of the distal-most part of the intermediate region. The intermediate region may be provided with a plurality of progressively tapered sections. In a further embodiment, the ultrasound transmission member has a proximal region, a distal end, and an intermediate region between the proximal region and the distal end. The intermediate region includes a proximal section, a central section, and a distal section, with the proximal and distal sections having dimensions that are larger than the dimension of the central section, and with the distal end of the ultrasound transmission member having a dimension which is larger than the dimension of the distal-most part of the distal section of the intermediate region. In yet a further embodiment, the distal end of the ultrasound transmission member has a configuration with two opposing straight sides connected by two curved sides, and the distal head includes a cylindrical bore for receiving the distal end of the ultrasound transmission member. A filler material is provided to fill the space in the cylindrical bore between the distal end of the ultrasound transmission member and the cylindrical bore.

The present invention further provides a sonic connector positioned on the proximal end of the ultrasound transmission member for connecting the ultrasound transmission member to a separate ultrasound generating device. The sonic connector has a proximal section for connection to the separate ultrasound generating device, and a tapered portion extending distally from a central portion, the tapered portion having a stem which couples the proximal end of the ultrasound transmission member. A housing is provided to house the sonic connector, the housing including a distal bore for retaining the stem and the proximal ends of the catheter body and the ultrasound transmission member. The housing further includes an O-ring positioned around the stem inside the distal bore in a position proximal to the proximal ends of the catheter body and the transmission member.

In another embodiment, the present invention provides a non-symmetrical balloon positioned adjacent the distal end of the catheter body such that inflation of the balloon will position the catheter body in an off-centered manner in a vessel. The catheter body is positioned at another off-centered position by rotating the catheter body by ninety degrees. The inflated balloon isolates a treatment region to which drugs may be delivered.

In yet another embodiment, the present invention provides the catheter body with a distal region that is more flexible that an intermediate region, and a proximal region that less flexible than the intermediate region.

In a further embodiment, the present invention provides an ultrasound transducer for generating ultrasound energy, and a transducer housing having a bore for housing the transducer. The transducer housing has an annular recess provided on an external housing wall, the annular recess having a beveled channel extending through the housing wall having an opening at an internal housing wall which is smaller than an opening at the external housing wall. At least one ball is positioned inside the beveled channel, and a sliding collar is positioned in a part of the annular recess. The connector housing is received inside the bore of the transducer housing with the proximal section of the sonic connector coupled to the distal end of the transducer. The sliding collar is then advanced inside the annular recess to depress the ball inside the beveled channel and to cause a portion of the ball to protrude out of the opening at the internal housing wall to engage the connector housing. The sliding collar may further include an annular bevel which covers, but does not depress, the ball before the sliding collar is advanced.

BRIEF DESCRIPTION OF THE DRAWINGS

FIGS. 8–9 are sectional side views of the distal end of ultrasound catheters that can be used with the system of FIG. 1, shown positioned inside a vessel and illustrating the use of various positioning balloons;

FIG. 9A is a cross-sectional view of the distal end of the catheter of FIG. 9 taken along line 9—9 thereof;

FIGS. 13 and 14 are cross-sectional views illustrating the use of the slidable gripping collar of the system of FIG. 1 to more securely connect the proximal end of the ultrasound catheter to the transducer.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
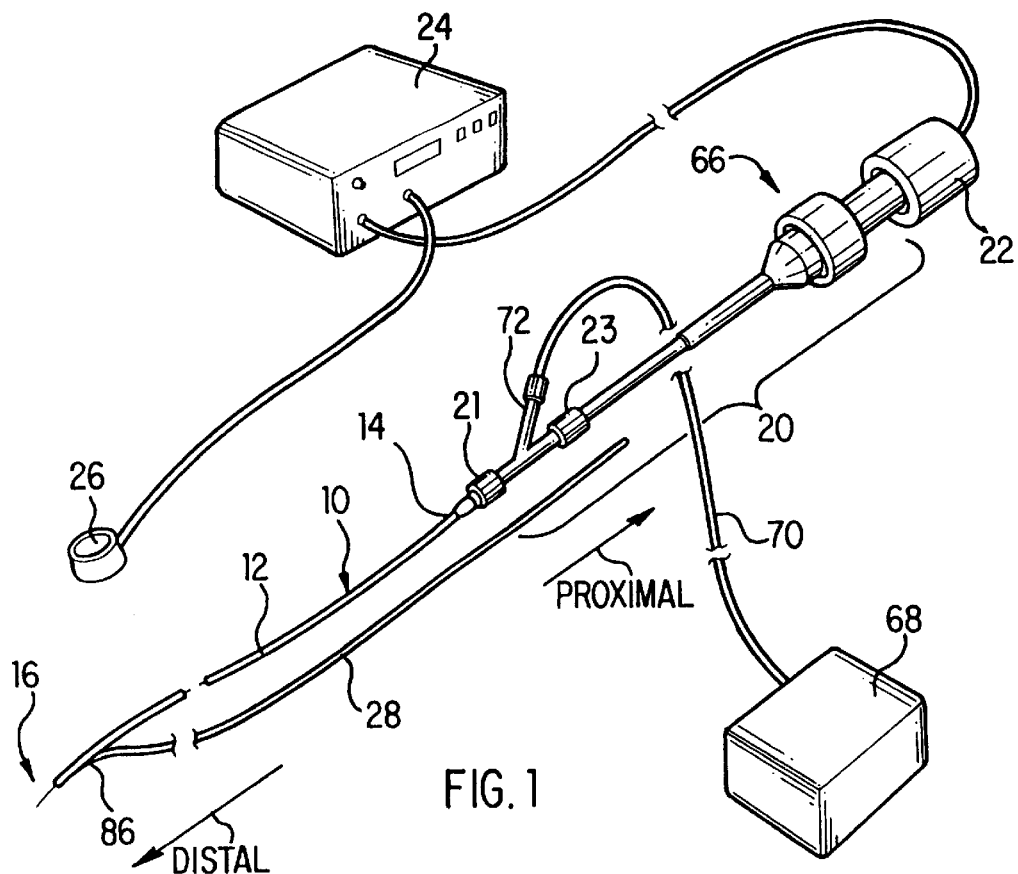
FIG. 1 is a perspective view of an ultrasound system according to the present invention.

FIG. 1 illustrates an ultrasound system according to the present invention for use in ablating or removing occlusive material inside the vessel of an animal or human being, or for massaging heart tissue during percutaneous myocardial revascularization. The ultrasound system includes an ultrasonic catheter device 10 which has a deflectable elongate catheter body 12 having a proximal end 14, a distal end 16, and defining at least one lumen extending longitudinally therethrough. The ultrasound catheter device 10 is operatively coupled, by way of a proximal connector assembly 20, to an ultrasound transducer 22. The ultrasound transducer 22 is connected to a signal generator 24. The signal generator 24 is provided with a foot actuated on-off switch 26. When the on-off switch 26 is depressed, the signal generator 24 sends an electrical signal to the ultrasound transducer 22, which converts the electrical signal to ultrasound energy. Such ultrasound energy subsequently passes through the catheter device 10 is delivered to the distal end 16 of the catheter body 12. A guidewire 28 may be utilized in conjunction with the catheter device 10, as will be more fully described below.

1. Configurations of the Distal End of the Catheter Device and the Ultrasound Transmission Member Several configurations for the distal end 16 of the catheter body 12 of the catheter device 10 are illustrated in FIGS. 2–7. In a preferred embodiment, the catheter body 12 is formed of a flexible polymeric material such as nylon (Pebax ) manufactured by Atochimie, Cour de Voie, Hauts Ve-Sine, FRANCE. The flexible catheter body 12 is preferably in the form of an elongate tube having one or more lumens extending longitudinally therethrough.

Figure 2:
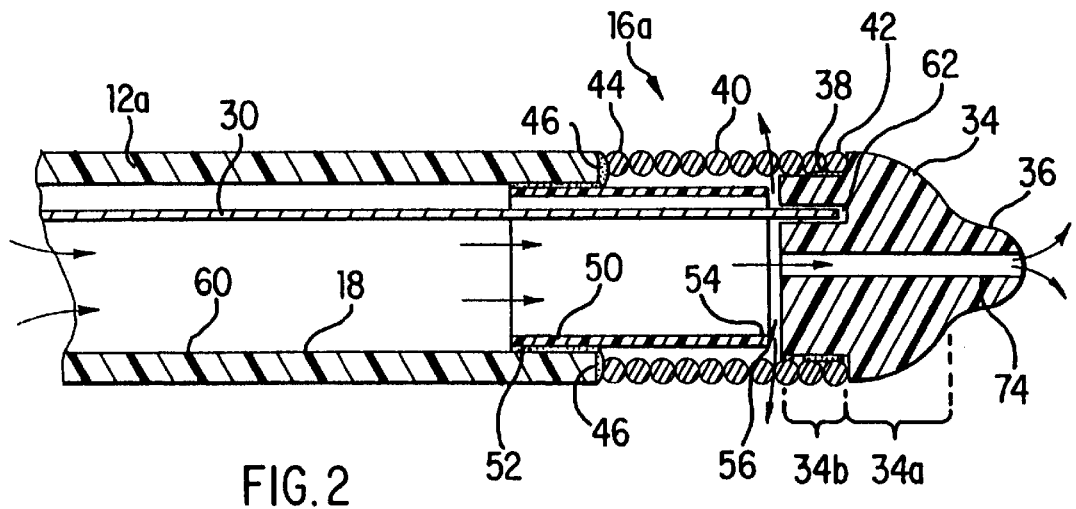
FIG. 2 is a cross-sectional view of the distal end of an ultrasound catheter that can be used with the system of FIG. 1 without a guidewire.

Referring to FIG. 2, the catheter body 12a has one lumen 18. Extending longitudinally through the lumen 18 of the catheter body 12a is an elongate ultrasound transmission member 30 having a proximal end which is connectable to the ultrasound transducer 22 such that ultrasound energy will pass through the ultrasound transmission member 30. As such, when the foot actuated on-off switch 26 operatively connected to the ultrasound transducer 22 is depressed, ultrasound energy will pass through the ultrasound transmission member 30 to the distal end 16a of the catheter body 12. More particularly, the ultrasound transmission member 30 serves to transmit the ultrasound energy from the proximal connector assembly 20 to a distal head 34 mounted on the distal end 16a of the catheter body 12a.

The distal head 34 has a substantially rigid member affixed to the distal end 16a of the catheter body 12a. In the embodiment shown, the distal head 34 has a generally rounded distal portion 34a, and a generally cylindrical proximal portion 34b. The distal portion 34a has a narrowed rounded tip 36 to create a stepped distal head configuration. The outer diameter of the proximal portion 34b is slightly less than the outer diameter of the distal portion 34a, defining an annular shoulder 38 to which a distal end 42 of a coil 40 is attached. The proximal end 44 of the coil 40 is attached to the open distal end 46 of the catheter body 12a such that the proximal portion 34b is not received inside the catheter body 12a but is spaced-apart therefrom. Preferably, the outer diameter of the coil 40 is about the same as the outer diameter of the catheter body 12a and the distal portion 34a, thereby forming a generally smooth outer surface at the juncture of the distal head 34, the coil 40 and the catheter body 12a, as shown in FIG. 2. An inner tube 50 is received inside the lumen 18 and coil 40, and has its outer surface 52 attached or fused to the inner wall 60 adjacent a portion of the distal end 46 of the catheter body 12a. Alternatively, the inner tube 50 can extend proximally inside lumen 18 as far as desired, depending on the degree of rigidity desired at the distal end 16a. A free distal end 54 of the inner tube 50 is not connected to the distal head 34, but instead is spaced-apart from the distal head 34 to form a spacing 56 therebetween. However, as explained in greater below, there are some instances where it is desirable to connect the distal end 54 of the inner tube 50 to the distal head 34 so that no spacing 56 is provided.

As an alternative, the proximal end 44 of the coil 40 can be attached to the inner wall 60 of the catheter body 12a so that the outer diameter of the coil 40 is less than the outer diameter of the catheter body 12a. According to this alternative, the coil 40 overlies the outer surface 52 of the inner tube 50, with the inner tube 50 attached to the coil 40 at the proximal end 44 of the coil 40.

As a further alternative, is it possible to provide the catheter body 12a and the inner tube 50 as a single piece which is narrowed and tapered towards the distal end, or which has a narrowed step configuration towards the distal end.

As yet another alternative, the inner tube 50 can be used as a connector between the coil 40 and the catheter body 12a, so that the proximal end 44 of the coil 40 is not directly attached to the open distal end 46 of the catheter body 12a, but is instead attached to the inner tube 50.

The attachment of the coil 40 to the distal head 34 and the catheter body 12a, and of the inner tube 50 to the catheter body 12a or coil 40, may be accomplished by any suitable manner. One manner is through the use of an adhesive which is applied to the interfacing surfaces to be attached. The adhesive may comprise any suitable adhesive, such as cyanoacrylate (e.g., Loctite Corp., Ontario, Canada or Aron Alpha , Borden, Inc., Columbus, Ohio) or polyurethane (e.g., Dymax , Dymax Engineering Adhesive, Torrington, Conn.). As an alternative to the use of adhesives, various mechanical or frictional connections, such as screw threads, lugs, or other surface modifications formed on one surface, can also be used, with corresponding grooves, detents, or surface modifications formed in the interfacing surface to be attached.

The distal head 34 may be formed of any suitable rigid material, such as metal or plastic. The distal head 34 is preferably formed of radiodense material so as to be easily discernible by radiographic means. Accordingly, the distal head 34 may preferably be formed of metal or, alternatively, may be formed of plastic, ceramic, glass, or rubber materials, optionally having one or more radiodense markers affixed thereto or formed therein. For example, the distal head 34 may be molded of plastic, such as acrylonitrile-butadiene-styrene (ABS) and one or more metallic foil strips or other radiopaque markers may be affixed to such plastic distal head 34 in order to impart sufficient radiodensity to permit the distal head 34 to be readily located by radiographic means. Additionally, in embodiments wherein the distal head 34 is formed of molded plastic or other non-metallic material, a quantity of radiodense fillers, such as powdered Bismuth or Barium Sulfate ($BaSO_4$) may be disposed within the plastic or other non-metallic material of which the distal head 34 is formed so as to impart enhanced radiodensity thereto.

The ultrasound transmission member 30 extends through the lumen 18 and the inner tube 50, and is inserted into a bore 62 which extends longitudinally into the proximal portion 34b of the distal head 34. The distal end of the ultrasound transmission member 30 is firmly held within the bore 62 by the frictional engagement thereof to the surrounding material of the distal head 34, or by other mechanical or chemical affixation means such as but not limited to weldments, adhesive, soldering and crimping. Firm affixation of the ultrasound transmission member 30 to the distal head 34 serves to facilitate direct transmission of the quanta of ultrasonic energy passing through the ultrasound transmission member 30 to the distal head 34. As a result, the distal head 34, and the distal end 16a of the catheter device 10, are caused to undergo ultrasonic vibration in accordance with the combined quanta of ultrasonic energy being transmitted through the ultrasound transmission member 30.

The coil 40 can be a single coil, a braid, a multilead coil, a cross-wound coil, a rounded wire coil, a flat wire coil, or any combination thereof. The coil 40 is preferably elastic and is made of a material having high elongation so as to conform to the configuration of the distal end 16 and to vibrate with the distal head 34 upon application of ultrasound energy. The coil 40 can be embedded inside a polymer jacket or coating, such as but not limited to PTFE, polyurethane, polyamide or nylon. The length of the coil 40 can range from 0.1 to 150 cm. Thus, the coil 40 provides several benefits. First, the coil 40 provides an elastic attachment of the distal head 34 to the catheter body 12a. Second, the coil 40 allows the distal head 34 to freely vibrate independent of the catheter body 12a. Third, the coil 40 provides an additional connection between the catheter body 12a and the distal head 34 since the coil 40 will hold the distal head 34 to the catheter device 10 in the event that the ultrasound transmission member 30 breaks or fractures.

The inner tube 50 is preferably formed from a soft and flexible material, such as but not limited to PTFE, polyurethane, polyamide or nylon. The inner tube 50 functions to provide a continuous flow of coolant along the transmission member 30 and irrigation output at the distal end 16, as explained in greater detail below. As a non-limiting example or alternative, the inner tube 50 can be omitted if the coils 40 are embedded inside a polymer jacket or coating. The embedded or coated coils 40 would form a tubular channel that would prevent loss of fluid flow therethrough, thereby rendering the inner tube 50 unnecessary.

In the preferred embodiment, the ultrasound transmission member 30 may be formed of any material capable of effectively transmitting the ultrasonic energy from the ultrasound transducer 22 to the distal head 34, including but not necessarily limited to metal, plastic, hard rubber, ceramic, fiber optics, crystal, polymers, and/or composites thereof. In accordance with one aspect of the invention, all or a portion of the ultrasound transmission member 30 may be formed of one or more materials which exhibit super-elasticity. Such materials should preferably exhibit super-elasticity consistently within the range of temperatures normally encountered by the ultrasound transmission member 30 during operation of the catheter device 10. Specifically, all or part of the ultrasound transmission member 30 may be formed of one or more metal alloys known as "shape memory alloys".

Examples of super-elastic metal alloys which are usable to form the ultrasound transmission member 30 of the present invention are described in detail in U.S. Pat. Nos. 4,665,906 (Jervis); 4,565,589 (Harrison); 4,505,767 (Quin); and 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member 30 of the present invention operates, any and all of which super-elastic metal alloys may be usable to form the super-elastic ultrasound transmission member 30.

In particular, the present invention provides an ultrasound transmission member 30, all or part of which may be made of a super-elastic metal alloy which exhibits the following physical properties:

| PROPERTY | UNIT | VALUE |
| --- | --- | --- |
| Nickel | Atomic Weight | Min. 50.50–Max. 51.50 |
|  | Weight Percent | Min. 55.50–Max. 56.07 |
| Titanium | % | Remainder |
| Total gas content (O, H, N) | % | 0.15 Max |
| Carbon Content | % | 0.010 Max |
| Maximum Tensile Strength | PSI | 220K |
| Elongation | % | 10–16 |
| Melting Point | Celcius | 1300–1350 |
| Density | g/cm$^3$ | 6.5 |

This alloy provides an ultrasound transmission member 30 that experiences minimum attenuation of ultrasound energy, and which has the ability to be navigated through the complex bends of tortuous vessels without experiencing any permanent deformation which would otherwise result in transmission losses.

Referring now to FIG. 1, the proximal connector assembly 20 of the catheter device 10 has an elongate, rigid body defining frontal, mid and rear portions. The frontal portion of the body is firmly connected to the proximal end 14 of the catheter body 12 via a threaded gripping member 21 engaged thereto. In this respect, the proximal end 14 of the catheter body 12 preferably has a flared configuration and includes an annular flange formed on the outermost end thereof which is brought into sealed engagement with the proximal connector assembly 20 when the gripping member 21 is threadably engaged to the body 12. The proximal end of the frontal portion is connected to the distal end of the mid-portion of the body via a second gripping member 23. To facilitate the aforementioned construction, threads are formed on the distal ends of the frontal and mid-portions of the proximal connector assembly 20. The extreme proximal end of the rear portion of the proximal connector assembly 20 is provided with a sonic connector assembly 66 which is configured to effect operative attachment of the proximal end of the ultrasound transmission member 30 to the horn of the ultrasound transducer 22. The sonic connector assembly or apparatus is preferably configured and constructed to permit passage of ultrasound energy through the ultrasound transmission member 30 with minimal lateral side-to-side movement of the ultrasound transmission member 30 while, at the same time, permitting unrestricted longitudinal forward/backward vibration or movement of the ultrasound transmission member 30. A more detailed description of the sonic connector assembly 66, and the operative attachment of the ultrasound transmission member 30 to the ultrasound transducer 22, are set forth below.

In the ultrasound system according to the present invention, an injection pump 68 is connected, by way of an infusion tube 70, to an infusion port or sidearm 72 in the frontal portion of the proximal connector assembly 20. The injection pump 68 is used to infuse coolant fluid (e.g., 0.9% NaCl solution) into and/or through the catheter device 10, and more particularly into the lumen 18 of the catheter body 12. Such flow of coolant fluid may be utilized to prevent overheating of the ultrasound transmission member 30 extending longitudinally through the lumen 18. Due to the desirability of infusing coolant fluid into the catheter body 12, at least one fluid outflow channel 74 extends longitudinally through the distal head 34 to permit the coolant fluid to flow from the lumen 18 out of the distal end 16a of the catheter body 12a. The coolant fluid can also flow out of the distal end 16a through the spacing 56 between the distal head 34 and the inner tube 50. Such flow of the coolant fluid through the lumen 18 serves to bathe the outer surface of the ultrasound transmission member 30, thereby providing for an equilibration of temperature between the coolant fluid and the ultrasound transmission member 30. Thus, the temperature and/or flow rate of coolant fluid may be adjusted to provide adequate cooling and/or other temperature control of the ultrasound transmission member 30.

In addition to infusing coolant fluid into and/or through the catheter device 10, the injection pump 68 may alternatively be utilized to infuse irrigation fluid into the lumen 18 of the catheter body 12a for purposes of removing debris from within the lumen of a vessel and/or forming a fluidic column to remove blood from the region of the distal head 34. As mentioned above, there may be instances where it is desirable to connect the distal end 54 of the inner tube 50 to the distal head 34 so that no spacing 56 is provided. One such instance is where an occlusion having hard material is encountered. In such a situation, it is desirable to direct all the irrigation fluid through the distal head 34 at the occlusion to provide better cavitation, rather than aspirating some of the irrigation fluid through the side spacing 56.

In addition to the foregoing, the injection pump 68 may be utilized to infuse a radiographic contrast medium into the catheter device 10 for purposes of imaging. Examples of iodinated radiographic contrast media which may be selectively infused into the catheter device 10 via the injection pump 68 are commercially available as Angiovist 370 from Berlex Labs, Wayne, N.J. and Hexabrix from Malinkrodt, St. Louis, Mo.

Although the catheter device 10 in FIG. 1 is illustrated as a "monorail" catheter device, the catheter device 10 can be provided as an "over-the-wire" catheter device without departing from the spirit and scope of the present invention. The structural and operative principles of "monorail" and "over-the-wire" guidewire techniques are well known to those skilled in the art, and are not further discussed herein.

Figure 3:
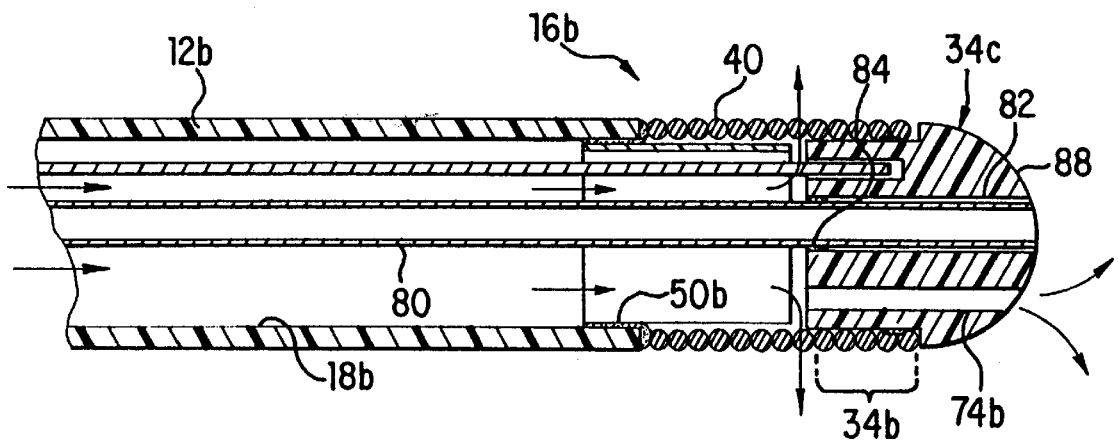
FIG. 3 is a cross-sectional view of the distal end of another ultrasound catheter that can be used with the system of FIG. 1 with a guidewire.

The catheter body 12a illustrated in FIG. 2 is deployed without the use of a guidewire. On the other hand, FIG. 3 illustrates a catheter body 12b that is deployed with the aid of a guidewire 28, and can be either a "monorail" or an "over-the-wire" catheter device. Catheter body 12b and its distal end 16b are essentially the same as catheter body 12a and its distal end 16a, except that a guidewire tube 80 defining a guidewire lumen extends through the lumen 18b, the inner tube 50b and a bore 82 formed through the distal head 34c. The guidewire tube 80 is bonded or attached at location 84 to the bore 82 according to one of the attachment or bonding methods described above. The fluid outflow channel 74b is offset from the center of the distal head 34c, but still communicates with the lumen 18b and inner tube 50b. In addition, the distal head 34c has a hemispherical configuration with a smooth and rounded distal surface 88, and does not have the narrowed tip 36 of distal head 34. However, the generally cylindrical proximal portion 34b is retained for supporting the coil 40. The guidewire tube 80 can extend along the length of the catheter body 12b if catheter device 10 is an "over-the-wire" catheter device. If catheter device 10 is a "monorail" catheter device, as shown in FIG. 1, the guidewire tube 80 terminates at a guidewire aperture 86 adjacent but slightly proximal from the distal end 16b of the catheter body 12b, at which the guidewire 28 exits the catheter body 12b.

The ultrasound transmission member 30 may be tapered, narrowed, or otherwise reduced in cross-sectional dimension within the catheter device 10 so as to decrease the rigidity of the ultrasound transmission member 30 and/or to cause amplification of the ultrasound transmitted to and from the distal head 34 thereof. FIGS. 4–7 illustrate several embodiments of the ultrasound transmission member 30 in combination with different distal head 34 configurations.

Figure 4:
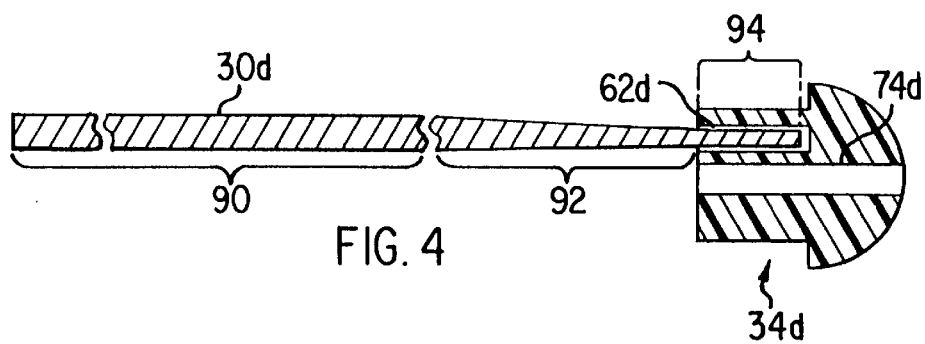
FIGS. 4–6 and 6A are partial cross-sectional views of the distal ends of ultrasound catheters that can be used with the system of FIG. 1 illustrating various configurations for the ultrasound transmission wire and the distal head.

For example, FIG. 4 shows a transmission member that has a proximal section 90 having a constant outer diameter, and a tapered mid-section 92 which gradually decreases in diameter from the proximal section 90 to a distal section 94 having a constant outer diameter. The distal section 94 is received into the bore 62d of the distal head 34d, which has a hemispherical configuration similar to the distal head 34c. Distal head 34d also has a central fluid outflow channel 74d.

Figure 5:
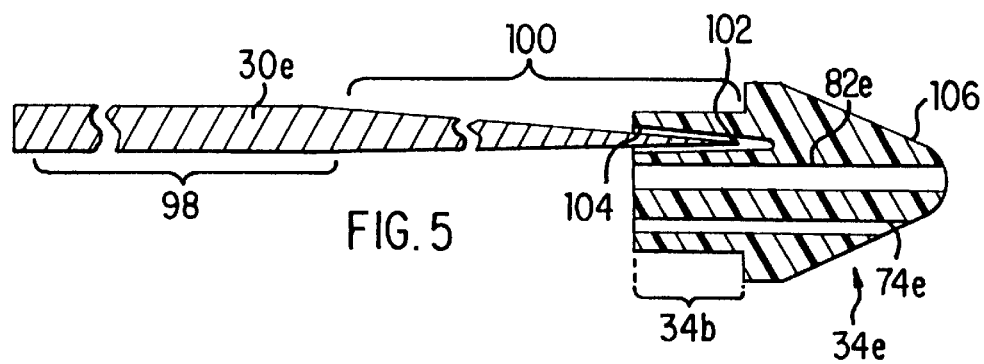

FIG. 5 shows a transmission member 30e that has a proximal section 98 having a constant outer diameter and a tapered distal section 100 which gradually decreases in diameter from the proximal section 98 until it reaches its conical distal tip 102. The distal section 100 is received into a conical bore or cavity 104 in the distal head 34e. Distal head 34e may be provided with a conical tip 106, and further includes an offset fluid outflow channel 74e and a central bore 82e for receiving a guidewire tube and/or guidewire. The tapered conical distal section 100 provides continuous and smooth amplification of ultrasound energy without steps, which helps improve the stability of the transmission member 30e.

Figure 7:
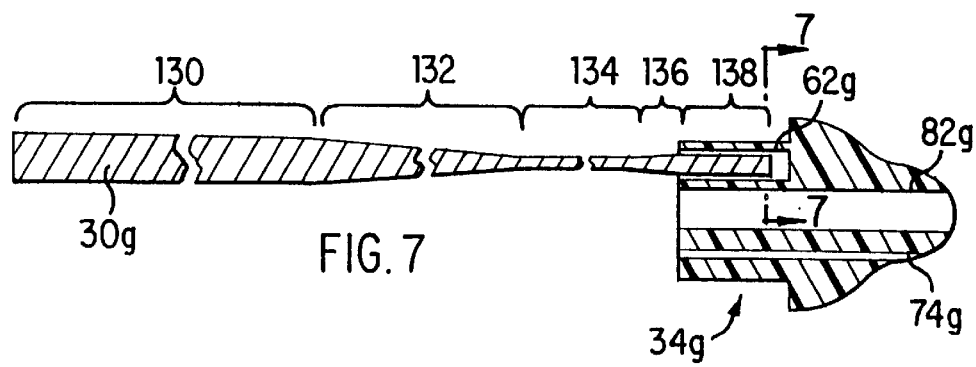
FIG. 7 is a partial cross-sectional view of the distal end of another ultrasound catheter that can be used with the system of FIG. 1 illustrating another configuration for the ultrasound transmission wire and the distal head.
Figures 6, 7A:
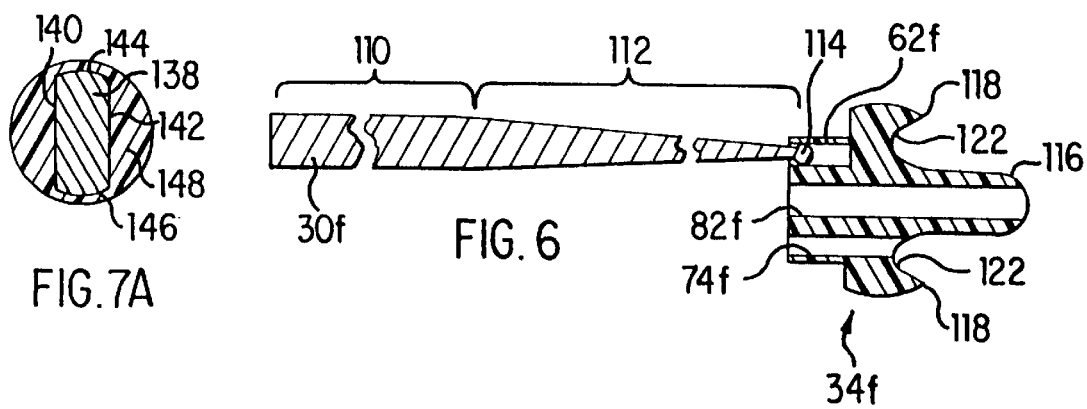
FIG. 7A is a cross-sectional view of the distal end of the catheter of FIG. 7 taken along line 7—7 thereof.

FIG. 6 shows a transmission member 30f that has a proximal section 110 having a constant outer diameter, and a tapered distal section 112 which gradually decreases in diameter from the proximal section 110 until it reaches a spherical distal tip or ball 114. The diameter of the ball 114 is preferably larger than the outer diameter of the distal-most portion of the tapered distal section 112. The ball 114 is received into, and is welded, bonded or attached to, the bore 62f of the distal head 34f. Distal head 34f is provided with a central narrowed tip 116 having a smooth and rounded tip, and an annular ridge 118 separated from the central tip 116 by a concave region 122. The annular ridge 118 may be provided with an annular cutting edge. Distal head 34f therefore allows energy to be intensified at certain points, such as at the narrowed tip 116 and along the ring-like ridge 118, and is therefore well-suited for use in certain applications, such as the ablation of harder occlusive material and calcified lesions. Distal head 34f further includes an offset aspiration or fluid outflow channel 74f terminating at the concave region 122, and a central bore 82f extending through the narrowed tip 116 for receiving a guidewire tube and/or guidewire. The ball 114 provides a larger cross-sectional dimension at the distal-most part of the transmission member 30f to tolerate stress associated with the attachment of the ball 114 to the distal head 34f.

Figure 6A:
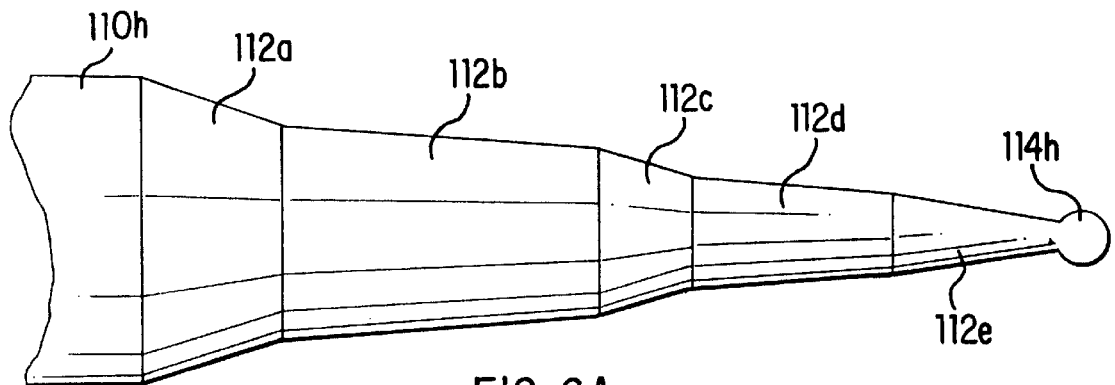

FIG. 6A shows a transmission member 30h that is very similar to the transmission member 30f illustrated in FIG. 6. The transmission member 30h has a proximal section 110h similar to proximal section 110, and a distal ball 114h similar to ball 114. However, instead of providing a single tapered distal section 112, the transmission member 30h provides a plurality of progressively tapered sections 112a–112e. The tapered sections nearer the proximal section 110h have a greater profile or dimension than the tapered sections nearer the distal ball 114h. The lengths each tapered section 112a–112e can range from 0.5 cm to 30 cm, and each tapered section 112–112e can have the same or different lengths. The progressively tapered sections 112a–112e improves ultrasound propagation through the transmission member 30h by providing higher amplitude and a smoother transition between the respective sections 112a–112e.

FIG. 7 shows a transmission member 30g that has a proximal section 130 having a constant outer diameter, and a first tapered section 132 which gradually decreases in diameter from the proximal section 130 until it reaches a central section 134. Central section 134 has a constant diameter and is connected at its distal end to a second tapered section 136 which gradually increases in diameter until it reaches a distal section 138 which has a constant dimension. As illustrated in FIG. 7A, the distal section 138 of the transmission member 30g has two straight lateral sides 140, 142 connected by top and bottom curved sides 144, 146, so that the distal section 138 does not assume the generally circular configuration of the proximal section 130. The distal section 138 is welded, bonded or attached inside a generally cylindrical bore 62g. The resulting space between the bore 62g and the distal section 138 may be filled up with a filler 148, which may be any absorbing material such as epoxy, rubber, glue, plastics or other suitable materials. The filler 148 functions to minimize the undesirable transverse motion of the distal section 138.

Providing the distal section 138 with the illustrated configuration improves the fatigue properties of the connection between the transmission member 30g and the distal head 34g, and therefore minimizes breakage of the member 30g because the filler 148 provides additional stability. In addition, by enlarging the transmission member 30g (at sections 136 and 138) from a narrowed section 134 facilitates greater efficiency in the transmission of ultrasound energy from the ultrasound transmission member 30g to the distal head 34g, improves the strength of the transmission member 30g, and minimizes breakage of the member 30g. Increasing the cross-section of the transmission member 30g provides a larger cross-sectional area to tolerate stress associated with the attachment of distal section 138 to the distal head 34g.

Distal head 34g has a stepped configuration similar to the distal head 34 in FIG. 2. Such a stepped configuration is useful in providing intensified ultrasound energy at the narrowed tip. A short and smaller tip is also less likely to perforate a vessel wall because of vessel elasticity and tip surface resistance. Distal head 34g also has a fluid outflow channel 74g offset from a central bore 82g for receiving a guidewire tube and/or guidewire.

Those skilled in the art will appreciate that any of the distal head 34 configurations illustrated in FIGS. 2–7 can be utilized with any of the transmission member 30 configurations illustrated in FIGS. 2–7, depending on the desired application and desired effects to be accomplished. In addition, the generally cylindrical proximal portion 34b is retained for each distal head 34 for supporting the coil 40.

2. Centering and Eccentric Balloons

The ultrasound catheter device 10 may be provided with one of different types of balloons for positioning the distal head 34 of the catheter device 10 at desired positions.

FIG. 8 illustrates a centering balloon 150 attached to the catheter body 12 adjacent the open distal end 46 of the catheter body 12 by using conventional balloon attachment methods. At least one lumen connects the interior of the centering balloon 150 with a source of balloon inflation fluid or other inflation media. When inflated by conventional balloon inflation methods, the balloon 150 centers the distal head 34 inside the vessel V. Since the softest part of an occlusion or obstruction OB is usually at its center, positioning the distal head 34 at this soft central region will make it easier for the catheter device 10 to cross the occlusion OB, or will provide an effective starting point for the application of ultrasound energy.

FIG. 9 illustrates an eccentric balloon 156 attached to the catheter body 12 adjacent the open distal end 46 of the catheter body 12 by using conventional balloon attachment methods. At least one lumen connects the interior of the balloon 156 with a source of balloon inflation fluid or other inflation media. When inflated, the balloon 156 positions the distal head 34 of the catheter device 10 in an off-centered position inside the vessel V. As shown in FIG. 9A, by rotating or torquing the catheter body 12 by ninety degrees, the distal head 34 can assume a plurality of radial positions 158a, 158b, 158c and 158d inside the vessel V. Thus, the eccentric balloon 156 can be used to enable the catheter device 10 to create an aperture (illustrated in phantom by 160) in the occlusion OB which is larger than the size of the distal head 34.

Both the balloons 150 and 156 can also be used in accordance with standard angioplasty principles to effect radial or other dilatation of the occlusion OB after the application of ultrasound energy thereto.

In addition, the balloons 150 and 156 can be used to enhance drug delivery to the vessel V at the site of the occlusion OB. As shown in FIGS. 8 and 9, the balloons 150 and 156 each operate to isolate a localized treatment region TR in the vessel V adjacent the occlusion OB. Drugs such as TPA, urokinase and streptokinase can be delivered via the infusion port or sidearm 72, through the lumen 18 and through the fluid outflow channel 74 and the spacing 56 to the treatment region TR. The delivery of such drugs can cause the surrounding vessel V to undergo smooth muscle relaxation due to the application of ultrasonic energy and the improved drug absorption by the tissue and cells.

3. Variable Catheter Body Flexibility

The catheter body 12 according to the present invention may also be provided with variable flexibility and profile. For instance, the distal portion of the catheter device 10 should preferably be more flexible because it must navigate through the tortuous vasculature inside a patient, while the proximal portion of the catheter device 10 should preferably be stiffer to facilitate handling during the procedure. Typically, at least two sections of different stiffness should be provided, a distal, more flexible, section (ranging from 0–50 cm) and a proximal, stiffer, section (ranging from 1–200 cm). Where the catheter body 12 is required to navigate tortuous vessel paths, three or more sections of different stiffness are preferably provided: a first distal section of greatest flexibility (ranging from 0–50 cm), a second central section of intermediate flexibility (ranging from 1–100 cm), and a third, stiffest, proximal section (ranging from 2–200 cm).

The flexibility of the catheter body 12 can also be varied by changing the profile thereof. For example, a portion of the catheter body 12 having a greater diameter would be less flexible than a portion of the catheter body 12 having a smaller diameter.

Figure 10:
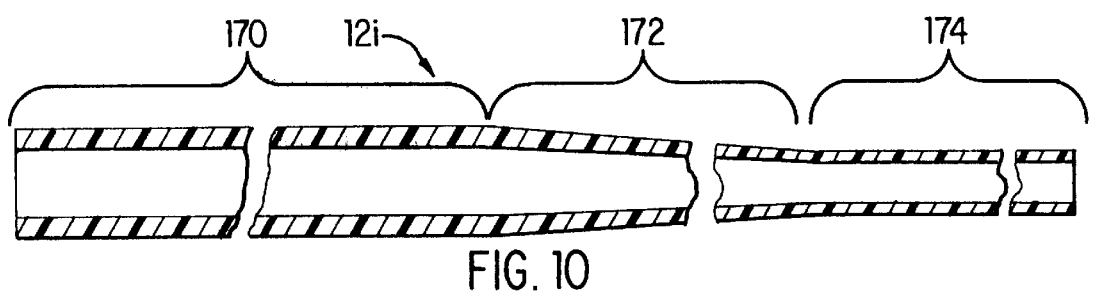
FIG. 10 is a sectional side view of a tapered catheter body of an ultrasound catheter that can be used with the system of FIG. 1.
Figure 11:
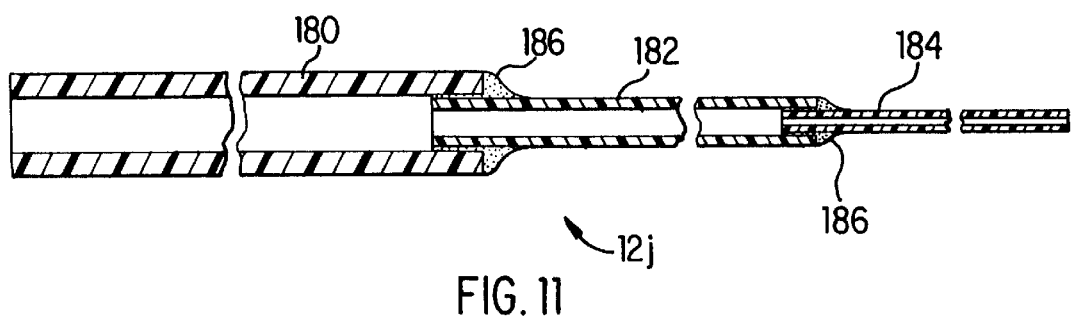
FIG. 11 is a sectional side view of a stepped catheter body of an ultrasound catheter that can be used with the system of FIG. 1.

FIGS. 10 and 11 illustrate ways in which the flexibility and profile of the catheter body 12 can be varied according to the present invention. In FIG. 10, the catheter body 12i is extruded or co-extruded as one integral piece having a proximal section 170, and a tapered mid-section 172 which gradually decreases in diameter (i.e., profile) from the proximal section 170 to a distal section 174. The thickness of the catheter body 12i also decreases gradually along the tapered mid-section 172 from its greatest thickness adjacent the proximal section 170 to its smallest thickness adjacent the distal section 174. The thickness of the proximal section 170 is greater than the thickness of the distal section 174. In addition, the thickness and/or profile of the catheter body 12i along the proximal and distal sections 170 and 174 can be constant throughout the respective sections 170, 174, or can be varied in each section 170 and/or 174.

In FIG. 11, the catheter body 12j may be provided with separate sections, including a proximal section 180, a mid-section 182, and a distal section 184, which are connected together by bonding, adhesives, RF fusing, heat fusing or other conventional attachment mechanisms at the attachment locations 186. Each section 180, 182 and 184 may be provided with a constant thickness throughout the respective sections, with the proximal section 180 having the greatest thickness, the distal section 184 having the smallest thickness, and the mid-section 182 having a thickness intermediate to the thicknesses of the proximal and distal sections 180, 184. In addition, the proximal section 180 preferably has the greatest outer diameter or profile, the distal section 184 has the smallest profile, and the mid-section 182 has a profile intermediate the profiles of the proximal and distal sections 180, 184. Alternatively, each section 180, 182, 184 can be provided with a tapered thickness and/or profile.

The flexibility of the sections 180, 182 and 184 may also be varied by using different material durometers. As a non-limiting example, the distal section 184 may have a low durometer (e.g., PBX 25–55), the mid-section 182 may have an intermediate durometer (e.g., PBX 35–63), and the proximal section 180 may have a higher durometer (e.g., PBX 55–85).

4. Sonic Connector Assembly and Slidable Gripping Collar

The present invention further provides a sonic connector assembly 66 that effectively connects the ultrasound transmission member 30 to the transducer 22 in a manner which reduces step sonic amplification and provides a smooth connection transition of the transmission member 30, thereby reducing the stress and fatigue experienced by the transmission member 30. The sonic connector assembly 66 has a sonic connector 200 housed inside the proximal bore 202 of a knob housing 204. The proximal bore 202 in knob housing 204 has a proximal opening 206 into which a transducer horn 208 (see FIGS. 13 and 14) may be inserted to engage the sonic connector 200. The sonic connector 200 has a central portion 210 having a vertical through-bore 212 which receives a locking pin 214. The locking pin 214 is inserted through an opening 216 in knob housing 204 and is received inside through-bore 212 to retain the sonic connector 200 at a pre-determined position inside proximal bore 202. The sonic connector 200 further includes a front tapered portion 218 extending distally from the central portion 210 and having a stem 220 which extends through a channel 222 in knob housing 204 connecting the proximal bore 202 with a distal bore 224. The stem 220 extends through channel 222 into the distal bore 224. The sonic connector 200 also has a threaded stem 226 extending proximally from the central portion 210 to permit the distal end 228 of the transducer horn 208 to be threadably screwed onto and releasably attached to the sonic connector 200.

The distal end of the stem 220 has a front bore 230 for receiving the proximal end of the ultrasound transmission member 30. The proximal end of the ultrasound transmission member 30 is connected to the stem 220 inside front bore 230 by welding, bonding, crimping, soldering, or other conventional attachment mechanisms. The rear portion of the proximal connector assembly 20 is threadably engaged or attached inside the distal bore 224. One or more O-rings 232, 234 are positioned about the stem 220 proximal to the proximal connector assembly 20.

The sonic connector assembly 66 minimizes undesirable transverse vibrations at a location where the ultrasound transmission member 30 experiences the greatest amount of stress. In particular, the location where the ultrasound transmission member 30 experiences the greatest amount of stress is at its connection with the sonic connector 200 inside the front bore 230. By positioning the O-rings 232, 234 over the stem 220 at a location immediately proximal to the connection at the front bore 230, the O-rings 232, 234 function to absorb or minimize the transverse vibrations from the transducer 22.

In addition, the gradual tapering or narrowing of the front tapered portion 218 provides gradual, rather than stepped, amplification of the transverse vibrations, thereby minimizing stress concentration and breakage of the transmission member 30 at its connection with the sonic connector 200.

The present invention further provides a slidable gripping collar assembly for fastening or connecting the ultrasound transducer 22 to the proximal connector assembly 20 and ultrasound transmission member 30 that mitigates the impact of undesirable loading on the connection between the transmission member 30 and the transducer resulting from forces applied during the bending, pushing, torquing and pressing of the catheter device 10 as the device 10 is being introduced and navigated along the patient's vasculature. Such undesirable loading may minimize the amount of ultrasound energy delivered to the distal end of the catheter device 10.

Referring to FIGS. 13 and 14, an annular sliding collar 250 is positioned for slidable movement over a distal portion of the transducer housing 252. In particular, the distal portion of the transducer housing 252 has an annular recess 254 in which the sliding collar 250 is slidably retained. Opposing beveled circular channels 256, 258 are provided in the wall of the transducer housing 252 between the recess 254 and the inner surface 260 of the housing 252, and as an integral part of the distal end of the recess 254. The channels 256, 258 are beveled so that they have a wider opening at the recess 254 than at the inner surface 260. Balls 262 and 264 are positioned inside the channels 256, 258, respectively. The diameter of the channels 256, 258 at the inner surface 260 is smaller than the diameter of the balls 262, 264 so that the balls 262, 264 cannot entirely pass through channels 256, 258 and fall into the housing 252. The front end of the collar 250 is provided with an annular bevel 266 so that the annular bevel 266 partially covers the balls 262, 264 to retain them inside the channels 256, 258 (see FIG. 13).

FIG. 13 illustrates the transducer housing 252 and the sonic connector 200 before they are connected. Prior to connection, the sliding collar 250 is positioned against the proximal wall of the recess 254, so that the annular bevel 266 partially covers the balls 262, 264 to retain them inside the channels 256, 258. Referring now to FIG. 14, the proximal stem 226 of the sonic connector 200 has been threadably engaged inside a threaded bore 268 at the distal end 228 of the transducer horn 208. The sliding collar 250 is then slid distally to compress the balls 262, 264 towards the inner surface 260. Since the balls 262, 264 have a spherical configuration, a portion of the balls 262, 264 extends pass the inner surface 260 into the interior of the transducer housing 252 and applies a compressive force against the knob housing 204 to securely retain the knob housing 204, and the sonic connector 200, inside the transducer housing 252.

To disengage the sonic connector 200 from the transducer 22, the collar 250 is slid proximally in the annular recess 254. Once the annular bevel 266 is aligned with the balls 262, 264, the balls 262, 264 will be naturally biased in a radial and outward manner, loosening their grip on the knob housing 204, and allowing the knob housing 204 to be removed from the transducer housing 252.

Although FIGS. 13 and 14 have illustrated the use of two balls 262, 264, those skilled in the art will appreciate that one, three or more balls can be used with the collar 250 without departing from the spirit and scope of the present invention.

Figure 12:
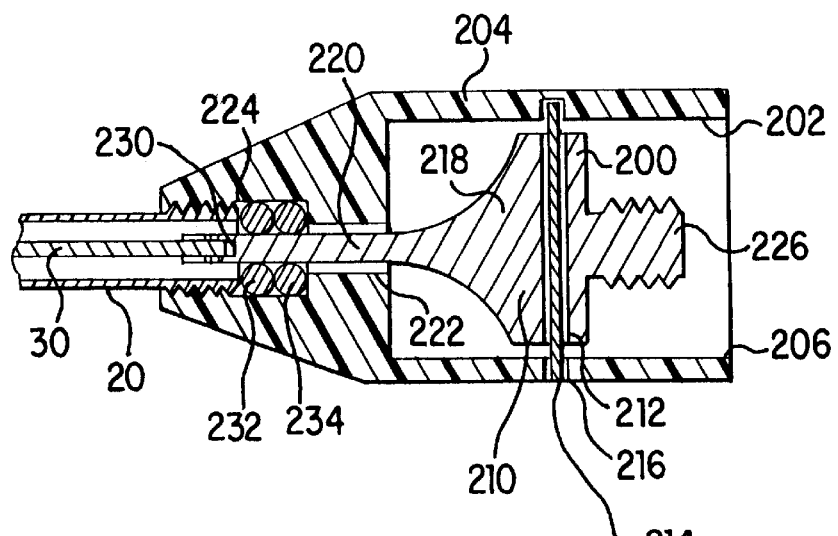
FIG. 12 is a cross-sectional view of the sonic connector assembly of the system of FIG. 1.

Thus, the ultrasound system according to present invention provides structural components that address the three general problems encountered by the known ultrasound systems and devices. For instance, effective transmission of ultrasound energy is achieved by the various transmission members 30 and distal end configurations described in connection with FIGS. 4–7, and the sonic connector 200 described in connection with FIG. 12. In addition, to facilitate accurate positioning of the ultrasound device through tortuous vessels, the present invention provides catheter bodies 12i and 12j with varying flexibility, thickness and profile, and ultrasound transmission members 30 having configurations that are able to navigate tortuous vessels. Further, the slidable gripping collar 250 minimizes loading on the connection between the transmission member 30 and the transducer.

In addition to the above, the present invention provides an improved material for the ultrasound transmission member 30 having properties that enhance its strength and performance. The present invention also provides ultrasound devices having coiled distal ends that improve the flexibility of the distal end. The present invention further provides ultrasound devices having balloons that help to effectively position the ultrasound device within a vessel, and to enhance drug delivery to the localized treatment region created by the balloon.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An ultrasound catheter comprising:
   an elongate flexible catheter body having a proximal end, a distal end and at least one lumen extending longitudinally therethrough;
   an ultrasound transmission member extending longitudinally through the lumen of the catheter body, the ultrasound transmission member having a distal end, and a proximal end connectable to a separate ultrasound generating device;
   a distal head positioned on the distal end of the ultrasound transmission member; and
   a coil having a proximal end connected to the distal end of the catheter body, and a distal end connected to the distal head, the coil defining a lumen communicating with the lumen of the catheter body.

2. The ultrasound catheter of claim 1, further comprising an inner tube extending inside the lumens of the catheter body and the coil, the inner tube having a proximal end connected to the catheter body and a free distal end, and defining a spacing between the distal end of the inner tube and the distal head.

3. The ultrasound catheter of claim 2, wherein the distal head has a fluid outflow channel provided therethrough and communicating with the lumens of the catheter body and the coil, and wherein drugs may be aspirated through the spacing and the fluid outflow channel.

4. The ultrasound catheter of claim 1, further comprising an inner tube extending inside the lumens of the catheter body and the coil, the inner tube having a proximal end connected to the catheter body and a distal end connected to the distal head.

5. The ultrasound catheter of claim 1, wherein the distal head has a generally cylindrical proximal portion with a bore for receiving the distal end of the ultrasound transmission member.

6. The ultrasound catheter of claim 1, further comprising a non-symmetrical balloon positioned adjacent the distal end of the catheter body such that inflation of the balloon will position the catheter body in an off-centered manner in a vessel.

7. The ultrasound catheter of claim 6, wherein the catheter body is positioned at another off-centered position by rotating the catheter body by ninety degrees.

8. The ultrasound catheter of claim 1, wherein the catheter body has a proximal region adjacent the proximal end, a distal region adjacent the distal end, and an intermediate region between the proximal region and the distal region, and wherein the flexibility of the catheter body increases from the proximal region to the intermediate region, and from the intermediate region to the distal region.

9. The ultrasound catheter of claim 1, wherein the ultrasound transmission member has a proximal region adjacent the proximal end and an intermediate region between the proximal region and the distal end, and wherein the intermediate region has a plurality of progressively tapered sections having dimensions that progressively decrease from adjacent the proximal region to the distal end.

10. The ultrasound catheter of claim 1, wherein the ultrasound transmission member has a proximal region adjacent the proximal end and a distal region adjacent the distal end, wherein the distal region is continuously tapered until it reaches a conical distal tip.

11. An ultrasound catheter comprising:
    an elongate flexible catheter body having a proximal end, a distal end and at least one lumen extending longitudinally therethrough;
    an ultrasound transmission member extending longitudinally through the lumen of the catheter body, the ultrasound transmission member having a distal end, and a proximal end connectable to a separate ultrasound generating device;
    a distal head positioned at the distal end of the ultrasound transmission member and having a generally cylindrical proximal portion with a bore for receiving the distal end of the ultrasound transmission member, wherein the distal head further includes a rounded distal portion having a narrowed tip extending distally therefrom; and
    a coil having a proximal end connected to the distal end of the catheter body, and a distal end connected to the distal head, the coil defining a lumen communicating with the lumen of the catheter body.

12. An ultrasound catheter comprising:
    an elongate flexible catheter body having a proximal end, a distal end and at least one lumen extending longitudinally therethrough;
    an ultrasound transmission member extending longitudinally through the lumen of the catheter body, the ultrasound transmission member having a distal end, and a proximal end connectable to a separate ultrasound generating device;
    a distal head positioned at the distal end of the ultrasound transmission member and having a generally cylindrical proximal portion with a bore for receiving the distal end of the ultrasound transmission member, wherein the distal head further includes a central narrowed tip, an annular ridge, and a concave region separating the central narrowed tip and annular ridge; and a coil having a proximal end connected to the distal end of the catheter body, and a distal end connected to the distal head, the coil defining a lumen communicating with the lumen of the catheter body.

13. An ultrasound catheter comprising:

an elongate flexible catheter body having a proximal end, a distal end and at least one lumen extending longitudinally therethrough;

an ultrasound transmission member extending longitudinally through the lumen of the catheter body, the ultrasound transmission member having a proximal end connectable to a separate ultrasound generating device, a proximal region adjacent the proximal end, a distal end, and an intermediate region between the proximal region and the distal end; and a distal head positioned at the distal end of the ultrasound transmission member;

wherein the intermediate region of the ultrasound transmission member has a plurality of progressively tapered sections having diameters that progressively decrease from adjacent the proximal region to the distal end, and wherein the distal end of the ultrasound transmission member has a diameter which is larger than the diameter of the distal-most part of the intermediate region.

14. The ultrasound catheter of claim 13, wherein the distal end of the ultrasound transmission member comprises a ball having a diameter which is larger than the diameter of the distal-most part of the intermediate region.

15. An ultrasound catheter comprising:

an elongate flexible catheter body having a proximal end, a distal end and at least one lumen extending longitudinally therethrough;

an ultrasound transmission member extending longitudinally through the lumen of the catheter body, the ultrasound transmission member having a proximal end connectable to a separate ultrasound generating device, a proximal region adjacent the proximal end, a distal end, and an intermediate region between the proximal region and the distal end; and a distal head positioned at the distal end of the ultrasound transmission member;

wherein the intermediate region of the ultrasound transmission member has a dimension which is smaller than the dimension of the proximal region, and wherein the distal end of the ultrasound transmission member has a dimension which is larger than the dimension of the distal-most part of the intermediate region; and wherein the distal end of the ultrasound transmission member has a configuration with two opposing straight sides connected by two curved sides, and wherein the distal head includes a cylindrical bore for receiving the distal end of the ultrasound transmission member, and a filler material for filling the space in the cylindrical bore between the distal end of the ultrasound transmission member and the cylindrical bore.

16. An ultrasound catheter comprising:

an elongate flexible catheter body having a proximal end, a distal end and at least one lumen extending longitudinally therethrough;

an ultrasound transmission member extending longitudinally through the lumen of the catheter body, the ultrasound transmission member having a proximal end and a distal end;

a distal head positioned on the distal end of the ultrasound transmission member;

a sonic connector positioned on the proximal end of the ultrasound transmission member for connecting the ultrasound transmission member to a separate ultrasound generating device, the sonic connector comprising a proximal section for connection to a separate ultrasound generating device, a central portion, and a tapered portion extending distally from the central portion, the tapered portion having a stem which couples the proximal end of the ultrasound transmission member; and a housing for housing the sonic connector, the housing including a distal bore for retaining the stem and the proximal ends of the catheter body and the ultrasound transmission member, the housing further including an O-ring positioned around the stem inside the distal bore in a position proximal to the proximal ends of the catheter body and the ultrasound transmission member.

17. The ultrasound catheter of claim 16, further comprising:

a connector housing for housing the sonic connector, the connector housing having an open proximal end;

an ultrasound transducer for generating ultrasound energy, the transducer having a distal end;

a transducer housing having a bore for housing the transducer, an internal housing wall and an external housing wall, the transducer housing further including an annular recess provided on the external housing wall, the annular recess having a beveled channel extending through the housing wall having an opening at the internal housing wall which is smaller than an opening at the external housing wall, the transducer housing further including a ball positioned inside the beveled channel, and a sliding collar positioned in a part of the annular recess;

wherein the connector housing is received inside the bore of the transducer housing with the proximal section of the sonic connector coupled to the distal end of the transducer; and wherein the sliding collar is advanced inside the annular recess to depress the ball inside the beveled channel and to cause a portion of the ball to protrude out of the opening at the internal housing wall to engage the connector housing.

18. The ultrasound catheter of claim 17, wherein the sliding collar includes an annular bevel which covers, but does not depress, the ball before the sliding collar is advanced.

19. An ultrasound system comprising:

an elongate flexible catheter body having a proximal end, a distal end and at least one lumen extending longitudinally therethrough;

an ultrasound transmission member extending longitudinally through the lumen of the catheter body, the ultrasound transmission member having a proximal end and a distal end; and a distal head positioned on the distal end of the ultrasound transmission member;

an ultrasound transducer for generating ultrasound energy, the transducer having a distal end;

a sonic connector positioned on the proximal end of the ultrasound transmission member for connecting the ultrasound transmission member to the transducer;

a connector housing for housing the sonic connector, the connector housing having an open proximal end; and a transducer housing having a bore for housing the transducer, an internal housing wall and an external housing wall, the transducer housing further including an annular recess provided on the external housing wall, the annular recess having a beveled channel extending through the housing wall having an opening at the internal housing wall which is smaller than an opening at the external housing wall, the transducer housing further including a ball positioned inside the beveled channel, and a sliding collar positioned in a part of the annular recess;

wherein the connector housing is received inside the bore of the transducer housing with the proximal section of the sonic connector coupled to the distal end of the transducer; and wherein the sliding collar is advanced inside the annular recess to depress the ball inside the beveled channel and to cause a portion of the ball to protrude out of the opening at the internal housing wall to engage the connector housing.

20. The ultrasound system of claim 19, wherein the sliding collar includes an annular bevel which covers, but does not depress, the ball before the sliding collar is advanced.

21. An ultrasound system comprising:

an elongate flexible catheter body having a proximal end, a distal end and at least one lumen extending longitudinally therethrough;

an ultrasound transmission member extending longitudinally through the lumen of the catheter body, the ultrasound transmission member having a proximal end and a distal end;

a distal head positioned at the distal end of the ultrasound transmission member;

an ultrasound transducer having a transducer horn; and a sonic connector positioned on the proximal end of the ultrasound transmission member for connecting the ultrasound transmission member to the transducer horn, the sonic connector comprising a proximal section for connection to the transducer horn, a central portion, and a tapered portion extending distally from the central portion, the tapered portion having a stem which couples the proximal end of the ultrasound transmission member.

* * * * *